United States Patent [19]

Malis

[11] 4,170,336
[45] Oct. 9, 1979

[54] SUSPENSION APPARATUS FOR OPERATING ROOM MICROSCOPE

[76] Inventor: Leonard I. Malis, 219-44 Peck Ave., Hollis Hills, N.Y. 11423

[21] Appl. No.: 861,359

[22] Filed: Dec. 16, 1977

[51] Int. Cl.$^2$ ............................................. G02B 23/16
[52] U.S. Cl. ....................................... 248/276; 248/324
[58] Field of Search ............... 248/276, 274, 278, 279, 248/282, 284, 285, 286, 121, 124, 324; 403/362, 169, 205; 350/83, 84, 85

[56] References Cited

U.S. PATENT DOCUMENTS

| | | | |
|---|---|---|---|
| 966,077 | 8/1910 | Bonta | 248/278 UX |
| 1,041,002 | 10/1912 | Bergh | 248/278 |
| 1,688,765 | 10/1928 | Veras | 248/278 X |
| 2,137,286 | 11/1938 | Herbig | 248/276 X |
| 3,790,249 | 2/1974 | Treace | 350/85 X |
| 3,809,454 | 5/1974 | Brambring | 350/85 X |
| 3,885,858 | 5/1975 | Hildemann | 350/85 X |
| 3,887,267 | 6/1975 | Heller | 350/85 |

FOREIGN PATENT DOCUMENTS

| | | | |
|---|---|---|---|
| 1901180 | 11/1969 | Fed. Rep. of Germany | 350/85 |
| 2320266 | 3/1974 | Fed. Rep. of Germany | 350/85 |

*Primary Examiner*—J. Franklin Foss
*Attorney, Agent, or Firm*—Kenyon & Kenyon

[57] ABSTRACT

A suspension arm and couplings are disclosed for supporting an operating room microscope. The suspension arm and couplings permit rotation of the microscope in the vertical plane up to angles of from about 140° to about 160° between the axis of vision of the microscope and the vertical. In the disclosed embodiment, the suspension arm is a one-piece C-shaped configuration provided with swivel joint couplings at each end thereof. One of the swivel joint couplings rotatably connects the C-shaped suspension arm to the remainder of a suspension system and the other swivel joint coupling suspends still another swivel joint coupling to which is connected the microscope. The swivel joint coupling connected to the microscope has a female part with a bore extending non-centrally therethrough for receiving the male part, a shaft, of a C-bracket which rotatably supports the microscope. The bore is disposed in the female part at an angle of from about 140° to about 160° from the vertical with reference to the mounted position of the swivel joint coupling.

8 Claims, 3 Drawing Figures

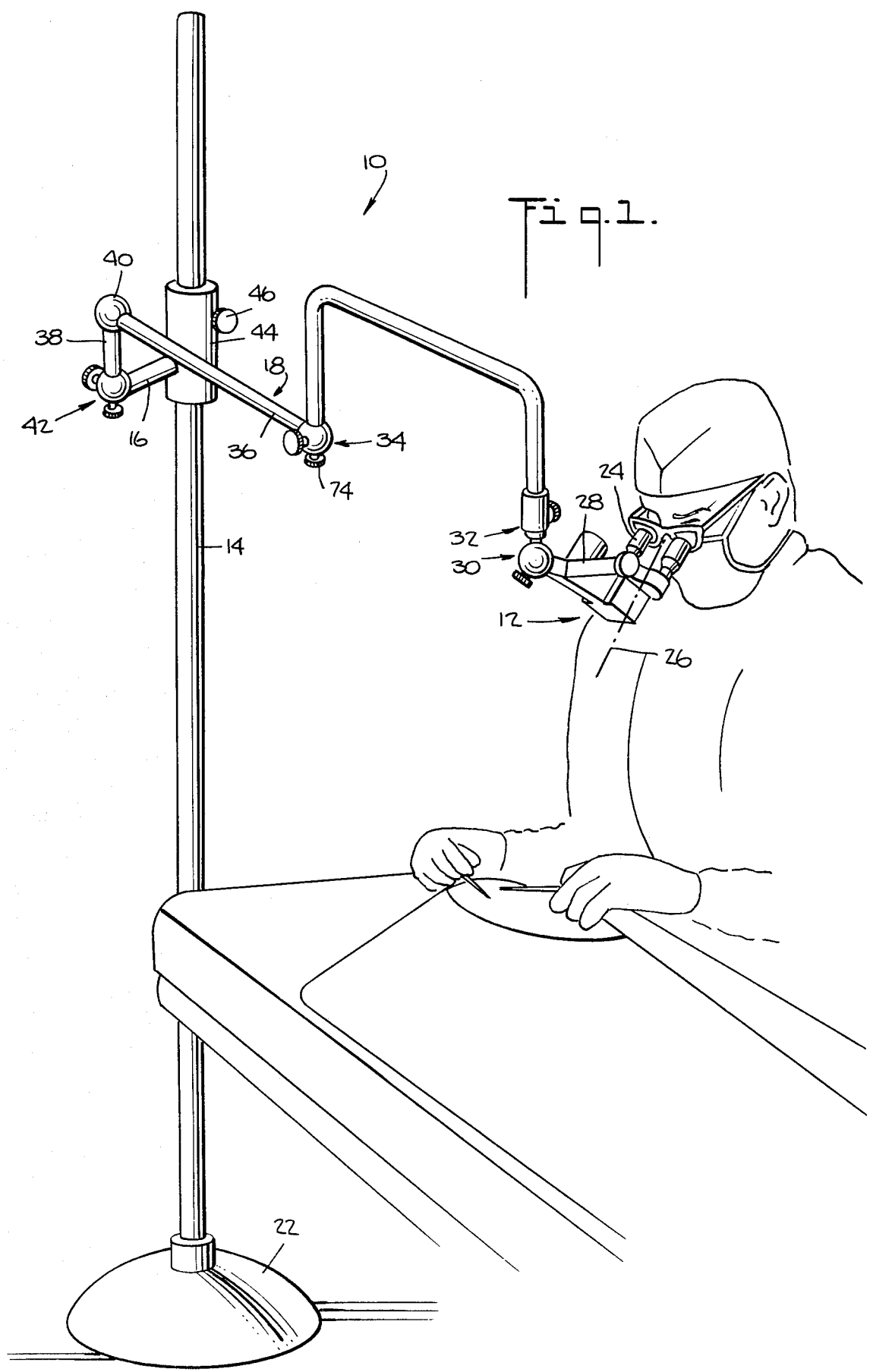

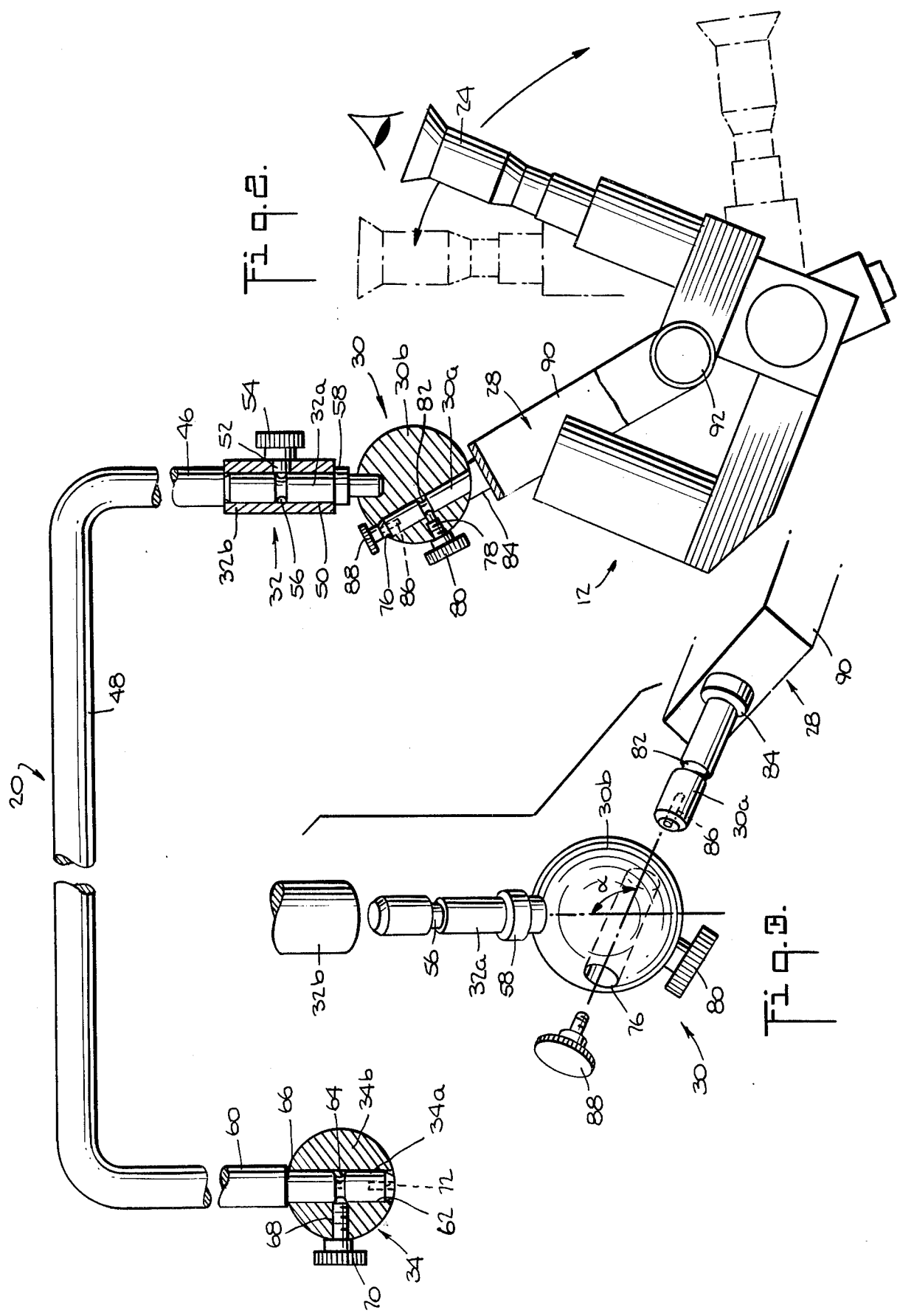

SUSPENSION APPARATUS FOR OPERATING ROOM MICROSCOPE

BACKGROUND OF THE INVENTION

1. Field of the Invention

The present invention relates to suspension systems for operating room microscopes and more particularly to a suspension arm and couplings for an operating room microscope.

2. Descriptions of the Prior Art

Microscopes used in operating rooms are supported by suspension systems which commonly include columns mounted on floorstands. The microscope is extended from and supported at the column by connecting arms and couplings which permit vertical and horizontal adjustment of the microscope. Several connecting arms are usually required in order to space the microscope from the column and provide freedom of movement for the surgeon, and several couplings are usually provided to permit adjustment of the microscope in given directions to quickly and securely position the microscope during use.

In the field of neurosurgery, it is often necessary to rotate the operating room microscope vertically so that the axis of vision forms an angle of about 150° with the vertical in order to use the microscope during certain procedures. However, certain suspension systems for prior art operating room microscopes permit only vertical rotation to an angle of about 120° between the axis of vision of the microscope and the vertical. Accordingly, such suspension systems are not generally adapted for procedures such as intracranial procedures which require th surgeon to look through the microscope upwards along an axis which forms an angle of greater than 120° with the vertical.

The present invention overcomes the deficiencies of the prior art and provides a suspension apparatus which permits rotation of an operating room microscope to angles between the axis of vision of the microscope and the vertical which exceed 120°.

SUMMARY OF THE INVENTION

It is an object of the present invention to provide an improved microscope suspension system which permits the microscope to be used over wider angles than prior art systems.

According to the present invention, a suspension apparatus for an operating room microscope is provided which permits rotation of the microscope in the vertical plane up to angles of from about 140° to about 160° between the axis of vision of the microscope and the vertical. The suspension apparatus includes an extension arm and coupling means rotatably connecting the microscope to the arm for rotation of the microscope over said angles of from up to about 140° to about 160°.

According to the invention in the disclosed embodiment thereof, the coupling means comprises first coupling means and second coupling means, the second coupling means supporting the first coupling means from the suspension arm for adjustable rotation of the first coupling means about the suspension arm. The microscope is suspended from a C-shaped bracket connected to the first coupling means which facilitates adjustable rotation of the bracket and microscope about the first coupling means, the axis of the C-shaped bracket (when secured in the first coupling means) being at an angle of from about 140° to about 160° from the vertical. The microscope is secured to arms of the C-shaped bracket and is adjustably rotatable about an axis extending between the arms. The first coupling means comprises a first lockable swivel joint which connects the C-shaped bracket with the second coupling means and forms a second lockable swivel joint. The suspension arm is C-shaped and of a one piece construction having the female part of the second lockable swivel joint at one end for receiving the male part of the first swivel joint. The female part or bore of the first swivel joint receives the male part of the C-shaped bracket and has its axis disposed at an angle with the vertical of from about 140° to about 160° with reference to the mounted position of the swivel joint. The male part of another lockable swivel joint is provided at the other end of the suspension arm for connecting the arm to the remainder of the suspension system.

In the preferred embodiment, the first and second coupling means rotatably couple the microscope to the C-shaped suspension arm for vertical rotation of the microscope through angles of up to about 150° between the axis of vision of the microscope and the vertical; the female part of the second swivel joint is in the form of a bore which extends non-centrally therein with the bore axis forming an angle of about 150° with the vertical in the mounted position of the swivel joint.

These and other aspects of the present invention will be more apparent from the following description of the preferred embodiment thereof when considered with the accompanying drawings.

BRIEF DESCRIPTION OF THE DRAWINGS

The present invention is illustrated by way of example and not limitation in the figures of the accompanying drawings in which like numerals refer to like parts and in which:

FIG. 1 is a perspective view depicting a microscope supported by the suspension apparatus according to the present invention being used by a surgeon in an operating room, FIG. 2 is a side elevation view, partly in cross-section, of the C-shaped suspension arm and swivel joint couplings according to the present invention depicting the microscope connected thereto; and FIG. 3 is an exploded perspective view depicting the swivel joint coupling according to the present invention connecting the C-bracket of the microscope to the C-suspension arm.

DESCRIPTION OF THE PREFERRED EMBODIMENT

FIG. 1 depicts suspension system 10 supporting an operating room microscope 12. Microscope 12 is supported and extended from column 14 of the suspension system by straight suspension arm 16, L-shaped suspension arm 18 and one-piece C-shaped suspension arm 20, column 14 being mounted on floorstand 22. The axis of vision of the microscope extends parallel to eyepieces 24 and is referenced by numeral 26. Microscope 12 is supported by C-shaped bracket 28 which is rotatably mounted in and forms part of swivel-joint 30. Similarly, swivel-joint 30 is rotatably mounted in and forms part of swivel joint 32 of C-shaped suspension arm 20. Another swivel-joint 34 rotatably connects C-shaped suspension arm 20 and L-shaped suspension arm 18, each arm forming part of the swivel joint. L-shaped suspension arm 18 includes a horizontal arm 36 and a vertical arm 38 which are rigidly secured together by threaded joint 40. L-shaped suspension arm 18 is rotatably mounted in straight suspension arm 16 by means of another swivel joint 42, each arm forming part of the swivel joint. Straight suspension arm 16 is rigidly mounted in collar 44 which is mounted to slide along column 14, a locking bolt 46 being provided to lock the collar in desired positions along the column. Each of the swivel joints permits rotation between a male part (30a in FIG. 2) and female part (30b in FIG. 2) forming the joint, the rotated parts being selectively locked in position by a locking bolt. In addition, collar 44 may be rotated about column 14 and selectively locked in a rotated position as well as moved along the column and locked in a vertical position by locking bolt 46.

As shown in FIG. 1, the suspension arms permit the microscope to be extended away from column 14, the swivel joints and collar being adjusted to position the microscope in a desired location over a patient. According to the preferred embodiment of the invention, the axis of vision of the microscope is adjustable on the C-shaped bracket over angles of up to about 150° from the vertical.

Referring to FIG. 2, C-shaped suspension arm 20 includes a vertical portion 46 extending at a right angle with center portion 48 of the arm and terminates with female portion 32b of swivel joint 32. Female portion 32b or collar has a bore 50 therein which is open at the lower end of the collar and is secured to the vertical part 46 at the upper end of the collar to close the bore thereat. A threaded hole 52 extends through the collar from the outside surface thereof to the bore, the hole being located in about the center of the collar and extending perpendicularly thereto. Threaded locking bolt 54 is screwed into hole 52, the shaft of the bolt extending into the bore. Shaft 32a forms the male portion of swivel joint 32 and is sized to slide and rotate within bore 50 in collar 32b when bolt 54 is loosened. Shaft 32a has an annular groove 56 about the circumference thereof spaced from the free end of the shaft a distance corresponding to the location of hole 52 so that the shaft of bolt 54 extends into the annular groove when fully inserted into the bore. The end of the locking bolt shaft is thereby located in the annular groove to lock shaft 32a in the bore against vertical movement and rotation.

Shaft 32a has a shoulder 58 which is positioned on the shaft to butt against the bottom of collar 32b when the shaft is fully inserted therein. To rotate shaft 32a, bolt 54 is loosened sufficiently to permit rotation while the shaft of bolt 54 extends into the annular groove and supports shaft 32a therein. This swivel-joint arrangement permits easy angular adjustment of the suspension arms.

C-shaped suspension arm 20 includes vertical portion 60 extending at a right angle from the center portion 48 and terminates in the male portion or shaft 34a of swivel joint 34. The spherical female portion 34b of the joint includes bore 62 extending through the center thereof. Shaft 34a is of smaller diameter than the vertical portion 60 and includes an annular groove 64. A shoulder 66 is formed along the circumference at which the diameter of vertical portion 60 changes and defines the length of the shaft which is approximately equal to the length of bore 62. An annular groove 64 is located on the shaft at approximately the center of bore 62 when shaft 34a is positioned therein. Threaded hole 68 extends toward the center of the spherical female part 34b and terminates at bore 62. The shaft of threaded locking bolt 70 is adapted to extend slightly into bore 62 when the bolt is screwed into hole 68. The end of the locking bolt shaft is thereby located in the annular groove to vertically and rotatably lock shaft 34a in bore 62 in a similar manner as described for joint 32. Shaft 34a includes a threaded axial bore 72 for receiving another locking bolt 74 therein (FIG. 1). Bolt 74 is provided to insure that shaft 34a is not separated from female part 34b if locking bolt 70 is inadvertently loosened and withdrawn completely from within bore 62.

As depicted in FIG. 1, joint 34 connects C-shaped suspension arm 20 and arm 18 while joint 32 connects C-shaped suspension arm 20 and swivel joint 30. As shown in FIGS. 2 and 3, the male or shaft portion 32a of swivel joint 32 is rigidly secured to and extends from the spherical female part 30b of swivel joint 30. Bore 76 of joint 30 is located in the spherical female part 30b and is disposed therein at an angle $\alpha$ with the axis of shaft 32a. When shaft 32a is secured in collar 32b (FIG. 2), bore 76 also forms the angle $\alpha$ with the vertical which may be from about 140° to about 160° and in the preferred embodiment is about 150°. Unlike bore 62 in spherical portion 34b of joint 34, bore 76 does not extend centrally through spherical part 30b. This permits placement of bore 76 at an angle of up to 160° from shaft 32a in the spherical part 30b. Threaded hole 78 extends through sphere 30b into bore 76 at about midway the length of the bore. The shaft of threaded locking bolt 80 when screwed into hole 78 extends into the bore. C-shaped bracket 28 includes the shaft 30a which forms the male portion of the swivel joint 30. Shaft 30a includes an annular groove 82 similar to groove 56, the groove and hole 78 being located so that the shaft of bolt 80 extends into the groove to lock shaft 30a in bore 76 in a similar manner as described for joint 32. Shaft 30a includes a collar 84 which butts up against spherical part 30b to locate groove 82 adjacent hole 78. A threaded axial bore 86 in shaft 30a and another locking bolt 88 is provided to secure shaft 30a to spherical part 30b when locking bolt 80 is loosened in a similar manner as described for shaft 34a. C-shaped bracket 28 includes a rod extending between arms 90 on which the microscope is rotatably supported. The microscope is locked in position on the rod by locking nut 92 which is threadedly secured to one end of the rod. The other end of the rod includes another nut or a bolt head to maintain the microscope on the rod and prevent removal of the rod from bracket 28. Tightening nut 92 urges the arms of bracket 28 towards one another to lock the microscope in the desired rotated position. Bracket 28 permits the microscope to be rotated from a position in which the axis of vision of the microscope is vertically down (most counterclockwise position in FIG. 2) to a position in which the axis of vision is parallel to shaft 30a of the C-bracket (most clockwise position in FIG. 2). Stop means are provided on the C-shaped bracket which prevents rotation of the microscope beyond the latter position (corresponding to an angle of about 150° with the vertical in the preferred embodiment shown in FIG. 2).

In accordance with the present invention, the surgeon may rotate the microscope to position the axis of vision of the microscope at angles of up to from about 140° to about 160° from the vertical. This extends the range of vision through the microscope over that of the prior art and enables the surgeon to look upwards through the microscope, thereby permitting the microscope to be used, for example, in intracranial procedures.

The advantages of the present invention, as well as certain changes and modifications of the disclosed embodiment thereof, will be readily apparent to those skilled in the art. It is the applicant's intention to cover by his claims all those changes and modifications which could be made to the embodiment of the invention herein chosen for the purpose of the disclosure without departing from the spirit and scope of the invention.

What is claimed is:

1. Suspension apparatus for rotatably supporting an operating room microscope comprising
   a C-shaped suspension arm having a central portion, an end portion disposed at a substantially right angle to the central portion and suspension arm coupling means disposed at said end portion, and
   microscope coupling means comprising a first swivel joint having a first female member which includes a bore disposed therein at an angle of from about 140° to about 160° from the vertical with reference to the mounted position of said first female member, said bore being adapted to rotatably receive a shaft which is connected to a member which is pivotably connected to the microscope,
   said suspension arm coupling means rotatably coupling said microscope coupling means to said end portion and comprising a second swivel joint having a second female member and a male member, one of said second female member and said male member being disposed at said end portion of said suspension arm and the other of said female member and said male member being connected to said first female member of said first swivel joint,
   whereby the microscope is adapted to being rotated in the vertical plane at angles of up to from about 140° to about 160° between the vertical and the axis of vision of the microscope.

2. The suspension apparatus as recited in claim 1, wherein said first female member is spherical in shape and said bore extends non-centrally within the spherical first female member.

3. The suspension apparatus as recited in claim 2, wherein said bore extends into said spherical first female member at an angle of about 150° from the vertical with reference to the mounted position of said spherical first female member, whereby the microscope is adapted to being rotated in the vertical plane at angles up to about 150° between the vertical and the axis of vision of the microscope.

4. The suspension apparatus as recited in claim 1, wherein said second female member is disposed at said end of said arm and said male member is connected to said first female member.

5. In a suspension system for an operating room microscope rotatably supported by a microscope mounting member, the system also including suspension arms and couplings, the improvement comprising a coupling which includes a first female member having a bore disposed therein at an angle of from about 140° to about 160° from the vertical with reference to the mounted position of the first female member in said suspension system, said bore bieng adapted to rotatably receive a shaft connected to the microscope mounting member, said coupling further comprising another member secured to the first female member and adapted to being rotatably coupled within said suspension system for rotatably supporting the first female member,
   whereby said microscope is adapted to being rotated in the vertical plane at angles of up to from about 140° to about 160° between the vertical and the axis of vision of the microscope.

6. The improvement as recited in claim 5, wherein said first female member is spherical in shape and said bore extends non-centrally therein.

7. The improvement as recited in claim 6, wherein said bore extends within said spherical first female member at an angle of about 150° with the vertical with reference to the mounted position of said spherical first female member whereby the microscope is adapted to being rotated in the vertical plane at angles of up to about 150° between the vertical and the axis of vision of the microscope.

8. The improvement as recited in claim 5, wherein said other member is a shaft adapted to being rotatably received in a female coupling member secured within the system.

* * * * *